(12) United States Patent
Liu et al.

(10) Patent No.: US 11,587,231 B2
(45) Date of Patent: Feb. 21, 2023

(54) COMPREHENSIVE DETECTION DEVICE AND METHOD FOR CANCEROUS REGION

(71) Applicant: Jiangsu University, Jiangsu (CN)

(72) Inventors: Zhe Liu, Jiangsu (CN); Kaifeng Xue, Jiangsu (CN); Yuqing Song, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 17/610,158

(22) PCT Filed: Jan. 21, 2021

(86) PCT No.: PCT/CN2021/073068
§ 371 (c)(1),
(2) Date: Nov. 10, 2021

(87) PCT Pub. No.: WO2022/110525
PCT Pub. Date: Jun. 2, 2022

(65) Prior Publication Data
US 2022/0301168 A1    Sep. 22, 2022

(30) Foreign Application Priority Data
Nov. 24, 2020   (CN) .......................... 202011327476.8

(51) Int. Cl.
*G06K 9/00* (2022.01)
*G06T 7/00* (2017.01)
(Continued)

(52) U.S. Cl.
CPC .......... *G06T 7/0016* (2013.01); *G06T 3/4046* (2013.01); *G06V 10/225* (2022.01);
(Continued)

(58) Field of Classification Search
CPC ................ G06T 7/0016; G06T 3/4046; G06T 2207/10081; G06T 2207/20076;
(Continued)

(56) References Cited

U.S. PATENT DOCUMENTS

2006/0228015 A1   10/2006 Brockway et al.
2010/0076296 A1    3/2010 Mittal et al.
(Continued)

FOREIGN PATENT DOCUMENTS

CN     101295309    10/2008
CN     107103187     8/2017
(Continued)

OTHER PUBLICATIONS

"International Search Report (Form PCT/ISA/210) of PCT/CN2021/073068," dated Aug. 24, 2021, pp. 1-5.
"Written Opinion of the International Searching Authority (Form PCT/ISA/237) of PCT/CN2021/073068," dated Aug. 24, 2021, pp. 1-4.

*Primary Examiner* — Xin Jia
(74) *Attorney, Agent, or Firm* — JCIP Global Inc.

(57) ABSTRACT

The present invention provides a comprehensive detection device and method for a cancerous region, and belongs to the technical field of deep learning. In the present invention, a cancerous region detection network is trained for preprocessed and annotated CT image data to predict bounding box coordinates of a cancerous region and a corresponding cancer confidence score; a clinical analysis network is trained for preprocessed clinical data with a cancer risk level to predict a cancer probability value of a corresponding patient; and a predicted cancer probability value is weighted to a predicted cancer confidence score to realize a comprehensive determination of the cancerous region. The present invention can detect a cancerous region with high accuracy and high performance.

7 Claims, 7 Drawing Sheets

(51) Int. Cl.
   *G16H 50/20* (2018.01)
   *G16H 30/40* (2018.01)
   *G06V 10/40* (2022.01)
   *G06V 10/82* (2022.01)
   *G06V 10/774* (2022.01)
   *G06V 10/22* (2022.01)
   *G06T 3/40* (2006.01)

(52) U.S. Cl.
   CPC ............ *G06V 10/40* (2022.01); *G06V 10/774* (2022.01); *G06V 10/82* (2022.01); *G16H 30/40* (2018.01); *G16H 50/20* (2018.01); *G06T 2207/10081* (2013.01); *G06T 2207/20076* (2013.01); *G06T 2207/20081* (2013.01); *G06T 2207/20084* (2013.01); *G06T 2207/30096* (2013.01); *G06V 2201/03* (2022.01)

(58) Field of Classification Search
   CPC . G06T 2207/20081; G06T 2207/20084; G06T 2207/30096; G06V 10/225; G06V 10/40; G06V 10/774; G06V 10/82; G06V 2201/03; G16H 30/40; G16H 50/20
   See application file for complete search history.

(56) References Cited

U.S. PATENT DOCUMENTS

| | | |
|---|---|---|
| 2014/0161337 A1 | 6/2014 | Raykar et al. |
| 2021/0090694 A1* | 3/2021 | Colley .................. G16B 40/00 |
| 2021/0201112 A1* | 7/2021 | Gauthier Melançon ..................... G06N 3/0427 |

FOREIGN PATENT DOCUMENTS

| | | | | |
|---|---|---|---|---|
| CN | 107945167 | | 4/2018 | |
| CN | 108564567 | | 9/2018 | |
| CN | 109145838 | | 1/2019 | |
| CN | 109242844 | | 1/2019 | |
| CN | 110236483 | | 9/2019 | |
| CN | 110573106 | | 12/2019 | |
| CN | 110648331 A | * | 1/2020 | ........... G06N 3/0454 |
| CN | 111127400 | | 5/2020 | |
| CN | 111584073 | | 8/2020 | |
| CN | 111862085 | | 10/2020 | |
| GB | 2597266 A | * | 1/2022 | ............... G06T 7/73 |
| WO | WO-2019245597 A1 | * | 12/2019 | ............... G06K 9/46 |

\* cited by examiner

COMPREHENSIVE DETECTION DEVICE AND METHOD FOR CANCEROUS REGION

CROSS-REFERENCE TO RELATED APPLICATION

This application is a 371 of international application of PCT application serial no. PCT/CN2021/073068, filed on Jan. 21, 2021, which claims the priority benefit of China application no. 202011327476.8, filed on Nov. 24, 2020. The entirety of each of the above mentioned patent applications is hereby incorporated by reference herein and made a part of this specification.

TECHNICAL FIELD

The present invention relates to the field of deep learning, and in particular to a comprehensive detection device and method for a cancerous region.

BACKGROUND

Due to a high fatality rate, cancer has long been a great threat to human life and health. In particular, liver cancer and lung cancer have always been cancers with a very high fatality rate in recent years. Generally, a patient, when discovering that he/she has related symptoms, is actually in the middle or advanced stage of cancer. Medical imaging diagnosis is an effective medical means for early screening of cancer. However, a cancerous region reflected on a medical image at an early stage of cancer is often small, and is difficult to be distinguished from surrounding non-cancerous regions. In addition, there are a large number of images produced during a screening process, and thus even radiologists with rich experience may have misdiagnosis and missed diagnosis due to a huge work load.

In view of the above situation, the computer-aided diagnosis (CAD) system has become the most powerful assistant for radiologists. The detection method based on traditional machine learning uses information about histogram of oriented gradients (HOG) and boundary operators to extract some low-level image features. However, this method depends heavily on manual intervention and prior knowledge and has a quite low execution speed. Fortunately, with the landmark 2012 as a turning point, medical imaging detection methods based on deep learning have become popular in recent years. Depending on the powerful feature extraction capability of a convolutional neural network (CNN), a deep learning method can handle higher-order semantic features than a traditional machine learning method, and has showed significant accuracy improvement, especially in the field of digital images.

According to different overall algorithms and frameworks for detection, the detection methods based on deep learning can be divided into anchor-based single-stage and two-stage detection methods and anchor-free keypoint detection methods. The anchor-based single-stage and two-stage detection methods use pre-defined prior boxes or anchor boxes, which is equivalent to sliding through all possible target locations on a feature map in an exhaustive manner. The anchor-based single-stage detection method strives to achieve forward propagation at one fling, and directly achieves regression and classification starting from a prior box, which has a high execution speed. The anchor-based two-stage detection method adopts a coarse-to-fine detection mechanism to filter out most of irrelevant anchor boxes on a background region through region proposals, which has a low detection speed, but a high accuracy. The anchor-free keypoint detection methods focus on outputting high-response features at key points (such as corner points and center points) of a target and further accurately locating a final detection box based on these points. However, in either of the two methods, the single-source input of medical images is fed to a CNN for forward inference detection, and an occurrence probability of false positives (a non-cancerous region is predicted as a cancerous region) is still high. In other words, the improvement only for a detection network can achieve limited accuracy improvement.

Existing related patents, such as Chinese patent CN201911201347.1 (a method and device for detecting a breast lesion) and Chinese patent CN201910520291.X (a method for detecting diabetic retinopathy (DR) based on a deep residual network), restrictively focus on using scanned medical images of a specified organ or tissue as an input of a neural network to realize the detection of a lesion. However, there is currently no relevant method to input clinical measurement information as an additional data source into a neural network for text analysis and use results thereof to further modify and improve an output of the neural network.

SUMMARY

In view of the shortcomings in the prior art, the present invention provides a comprehensive detection device and method for a cancerous region. In the present invention, a predicted cancer probability value is weighted to a predicted cancer confidence score to achieve a comprehensive determination of a cancerous region, thereby achieving the detection of the cancerous region with high accuracy and high performance.

The present invention achieves the above technical objective through the following technical means.

A comprehensive detection method for a cancerous region is provided, specifically including:

acquiring CT image data and clinical data;

preprocessing the CT image data and the clinical data to convert the data into a format that can be input by an applicable cancer detection and analysis sub-module;

training a cancerous region detection network for preprocessed and annotated CT image data to predict bounding box coordinates of a cancerous region and a corresponding cancer confidence score;

training a clinical analysis network for preprocessed clinical data with a cancer risk level to predict a cancer probability value of a corresponding patient;

weighting a predicted cancer probability value to a predicted cancer confidence score to realize a comprehensive determination of a cancerous region, wherein a threshold value of 0.5 is set for the cancer probability value, a difference between the cancer probability value and the threshold is stretched into an interval (0, 1), then an exponential function $e^x$ is used to acquire a scale factor, and the scale factor is applied to the cancer confidence score to achieve incentive or penalty for the confidence score;

screening out repeated detection boxes for a same cancerous region and decoding a bounding box to output the cancerous region and a corresponding confidence score of a current patient.

Further, the incentive or penalty is obtained by the following formula:

$$conf = (P(\text{object}) * IOU(pred, gtBox)) \cdot f(e^{\sigma(P_{CA})})$$

-continued $$IOU(pred, gtBox) = \frac{pred \cap gtBox}{pred \cup gtBox}$$

wherein (P(object)*IOU(pred,gtBox)) is a confidence score output; P(object) is an occurrence probability of a cancerous region in a prediction box; IOU represents a fit degree of a prediction box pred with a true box gtBox; $f(e^{\sigma(P_{CA})})$ is a scale factor; $P_{CA}$ is a cancer probability value of a patient; and σ represents a normalization operation, that is, a difference between the cancer probability value and the threshold is stretched into an interval (0, 1).

Further, the cancer confidence score is retained by reading all vectors with a length of 5, and the length of 5 refers to 4 bounding box attributes and 1 target confidence score.

Further, the detection network and the clinical analysis network are both CNNs, and the training of the CNNs is achieved by a directional propagation learning method and a random gradient descent method.

Further, the detection network forms different feature levels similar to a pyramid through a plurality of up-sampling operations and lateral connections corresponding to a down-sampling stage of feature extraction, and then achieve the detection of a cancerous region at the different levels; each pyramid level includes a plurality of down-sampling, and each level is composed of n residual blocks before down-sampling; and the residual block includes two components that have the three operations of convolution, batch normalization, and activating function cascaded together, and an internal input of the residual block is directly connected to an output.

Further, the clinical analysis network includes input and quantification, a hidden layer, and an output layer.

A comprehensive detection device for a cancerous region is also provided, including a data acquisition module, a processing module, and a visualization module, wherein the data acquisition module is configured to acquire CT image data and clinical data from a daily workflow of a clinician to train a neural network;

the processing module is configured to extract hidden features in the data and output a prediction;

the visualization module is configured to output the cancerous region and a corresponding confidence score of a current patient;

the processing module includes a cancer detection and analysis sub-module, a prediction result weighting sub-module, and a detection result post-processing sub-module; the cancer detection and analysis sub-module is configured to input acquired data into a CNN to generate a corresponding predicted value; the prediction result weighting sub-module is configured to fuse a cancer probability value after feature extraction and a predicted cancer confidence score; and the detection result post-processing sub-module is configured to screen out repeated detection boxes for a same cancerous region and decode a bounding box.

A computer-readable storage medium is also provided, wherein a computer program stored in the computer-readable storage medium enables a processor to perform the comprehensive detection method for a cancerous region described above.

Beneficial effects of the present invention: In the present invention, a cancerous region detection network is trained for preprocessed and annotated CT image data to predict bounding box coordinates of a cancerous region and a corresponding cancer confidence score; a clinical analysis network is trained for preprocessed clinical data with a cancer risk level to predict a cancer probability value of a corresponding patient; and a predicted cancer probability value is weighted to a predicted cancer confidence score to realize a comprehensive determination of a cancerous region. A cancer prediction result of clinical data is fully fused into a cancer confidence score by weighting, such that a detection network originally with a limited accuracy will be more "confident" when encountering an ambiguous cancerous region and thus a cancerous region can be detected with high precision and high performance. The present invention simulates a comprehensive diagnosis process to determine whether a suspected cancerous region of a patient is cancerous at an early stage clinically, such that the whole CAD system designed using the comprehensive detection method for a cancerous region of the present invention becomes the most powerful assistant for radiologists.

DETAILED DESCRIPTION OF THE EMBODIMENT

The present invention will be further described below in conjunction with the accompanying drawings and specific examples, but the protection scope of the present invention is not limited thereto.

Figure 1:
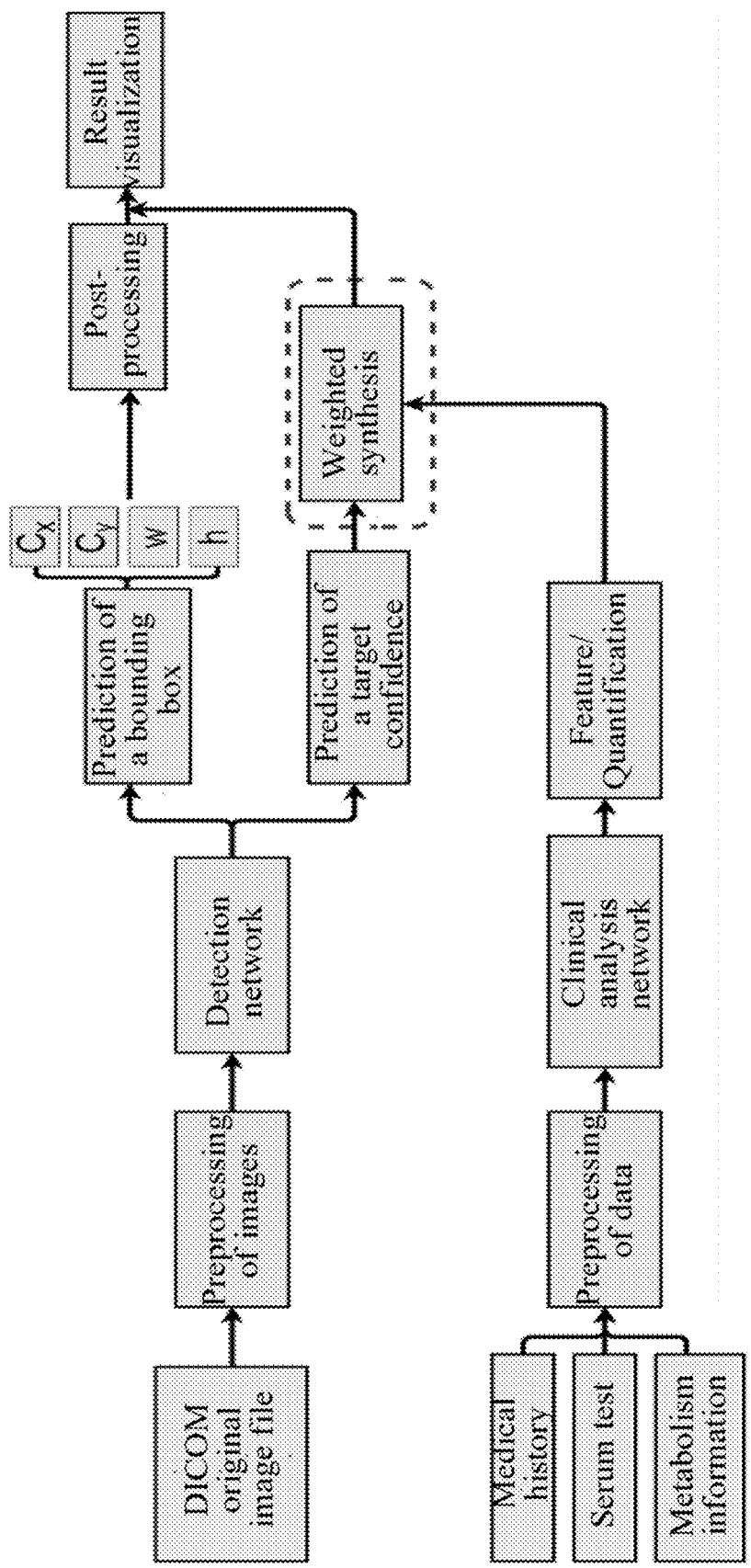
FIG. 1 is a flow chart of the comprehensive detection method for a cancerous region according to the present invention.

As shown in FIG. 1, a comprehensive detection method for a cancerous region is provided in this example, and with liver cancer as an example, the comprehensive detection method specifically includes the following steps.

Step (1). Acquisition of Image Data and Clinical Data

When the image data are acquired, an advanced and high-accuracy computed tomography (CT) instrument is used to generate a large number of CT scan slices of the abdomen; the clinical data are acquired from daily work records of clinicians; and when the image data and clinical data are entered into a database or another storage management system (such as the storage data set in FIG. 7), it is necessary to ensure that there is a one-to-one correspondence between information and each patient, thereby facilitating the subsequent use by a cancer detection and analysis sub-module.

For example, for a specified patient A, each volume of data saved for each CT scan should be systematically stored in a folder named "A_S*_V*", wherein "S*" corresponds to an index of the number of scans and "V*" represents a volume number, and slices generated in each volume are also named and placed in the folder according to a scanning order; and the clinical data of the patient A are classified into different folders according to medical history, serum test information, physiological characteristics, and the like of the patient. The above operations are conducted to facilitate the subsequent processing and display of specified patient data by a processing module and a visualization module.

Not all acquired image slice data need to be retained. In a volume of scanned slices, some beginning and end slices often do not cover the liver (or another specified organ or tissue), and thus these worthless slices need to be screened out.

Step (2). Cancer Detection and Analysis

Step (2.1). For CT image data, a professional physician selects a cancerous region (or an annotation) through a rectangular box, and information of an annotated rectangular box should be recorded in a .txt, .xml, or .json file with the same name as the image data, which should strictly include a set of data composed of ($C_x$, $C_y$, w, h) or (Xmin, Ymin, Xmax, Ymax) attributes (either of the two can uniquely determine a position of a rectangular box), wherein ($C_x$, $C_y$) represent coordinates of a center point, (w, h) represents a width and a height of a rectangular box, (Xmin, Ymin) represents coordinates of an upper left corner point, and (Xmax, Ymax) represents coordinates of a lower right corner point.

For the clinical data, a clinician determines a cancer risk level based on rich experience. In order to minimize the extra working pressure on clinicians, the cancer risk level is only classified as high, medium, and low.

Then the CT image data and the clinical data are preprocessed and converted into an expected input form suitable for the subsequent training of a neural network.

Preprocessing of CT image data: The original scan slice format directly generated by a machine is DICOM (.dcm), which cannot be directly fed into a neural network as an input for training or prediction. Therefore, the format needs to be converted with the help of Python related libraries into a .jpg or .png image format, or may be converted into a two-dimensional array. In a conversion process, the limitation on window levels and a window width (i.e., the limitation on a Hounsfield unit (HU) value) corresponding to the liver (or another organ or tissue) needs to be concerned to obtain a maximum contrast with surrounding organs (to make the liver revealed as much as possible). For the liver, according to experience of professional radiologists, the HU value is limited in an interval of [−100, 240], wherein −100 and 240 indicate the window levels and a distance between the two ends indicates the window width. A defined formula is as follows:

$$HU_{i,j} = \begin{cases} -100, & \text{if } HU_{i,j} \leq -100 \\ 240, & \text{if } HU_{i,j} \geq 240 \\ PV_{i,j} * \text{slope} + \text{intercept}, \end{cases}$$

wherein $HU_{i,j}$ represents an HU value at a pixel point (i, j), $PV_{i,j}$ represents a pixel value at a position (i, j) of the original DICOM image, and slope and intercept represent a slope value and an intercept value for a corresponding linear operation.

Preprocessing of clinical data: The digital information in the clinical data is further quantified, and a deviation of a measured clinical value from a normal value is used as an index to measure a severity of a patient under a single index. For example, an alpha-fetoprotein (AFP) level is an index with high reference value for liver cancer. If a measured value of a person is not in a normal range (i.e., ≥25 ng/mL), the larger the deviation from this value, the greater the initial value given, and a specific change range needs to be determined by an experienced clinician. If a measured value is within a normal range, a small non-zero value (such as 0.001) is given as an initial value fed into the subsequent neural network. It should be noted that the initial value is set above merely to ease the difficulty of subsequent initial training of a neural network.

Step (2.2). A cancerous region detection network is trained for preprocessed and annotated CT image data. Since a cancerous region occupies a small area on an entire CT image, with the hardware computing power conditions allowed, the entire image can be properly enlarged through bilinear interpolation. The enlargement operation should follow a specified rule and is not conducted arbitrarily, and a pixel value for the enlargement is usually an integer multiple of 64 or 128, which is determined by a down-sampling ratio of the subsequent detection network. An enlarged image is fed to a detection network for training. Similarly, a clinical analysis network is trained for preprocessed clinical data with a final cancer risk level. Both the detection network and the clinical analysis network are CNNs.

Step (2.2.1). Training of CNN

Under a pytorch framework of the Ubuntu system, preprocessed data of 6,000 abdominal CT images are divided into a training set, a validation set, and a test set at a ratio of 7:2:1; according to the number of persons involved in the source of clinical data acquisition and the above ratio, the clinical data are also divided into a training set, a validation set, and a test set correspondingly; a neural network is trained by a directional propagation learning algorithm in combination with a random gradient descent method; according to a loss value calculated based on one forward inference, back propagation is conducted to iteratively update a weight and a bias (if any) of each parameter layer of the neural network; and after a specified number of training iterations, if a loss on the training set and a loss on the validation set tend to converge, the training of the neural network is completed. It should be noted that the detection network and the clinical analysis network can be trained separately without any coupling.

Figure 2:
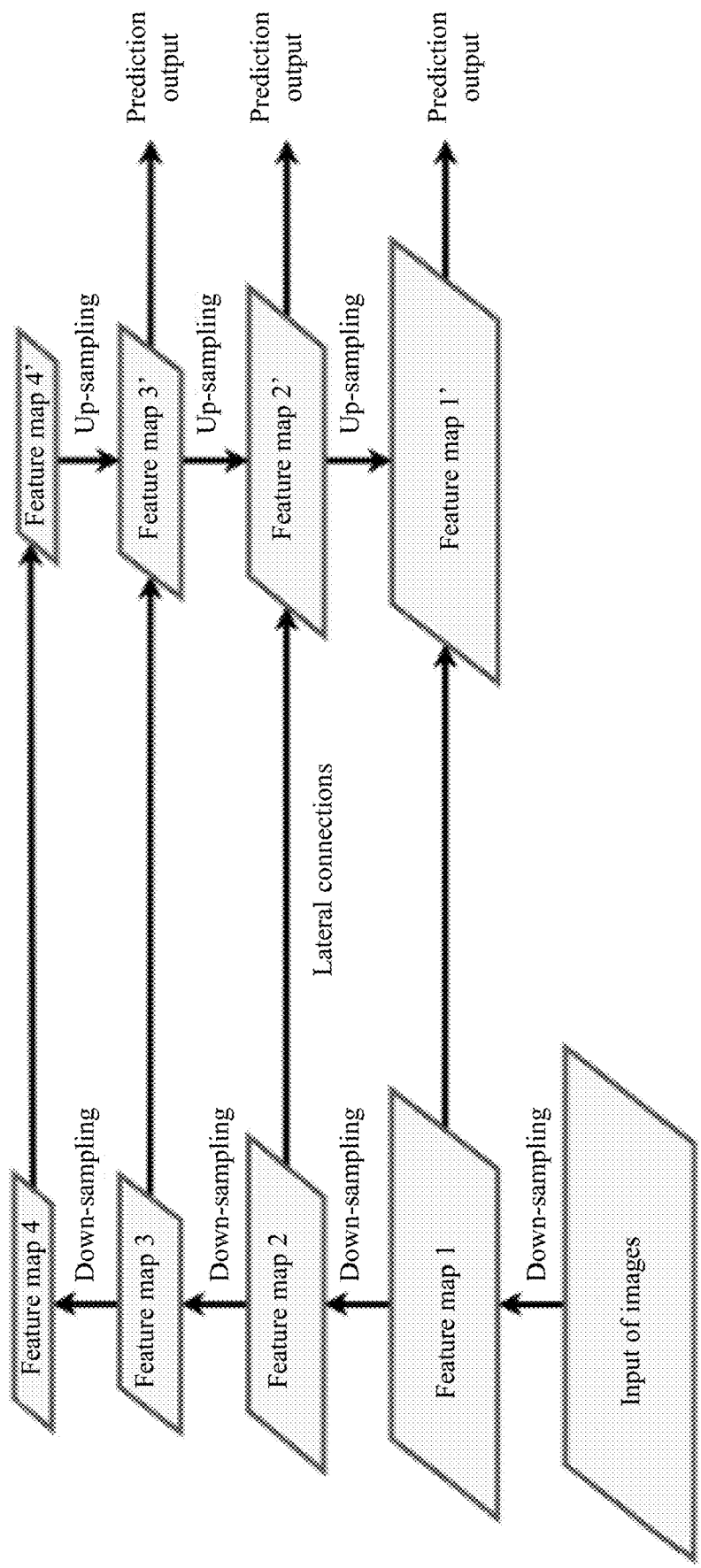
FIG. 2 is a schematic diagram of design steps of the detection network according to the present invention.
Figure 3:
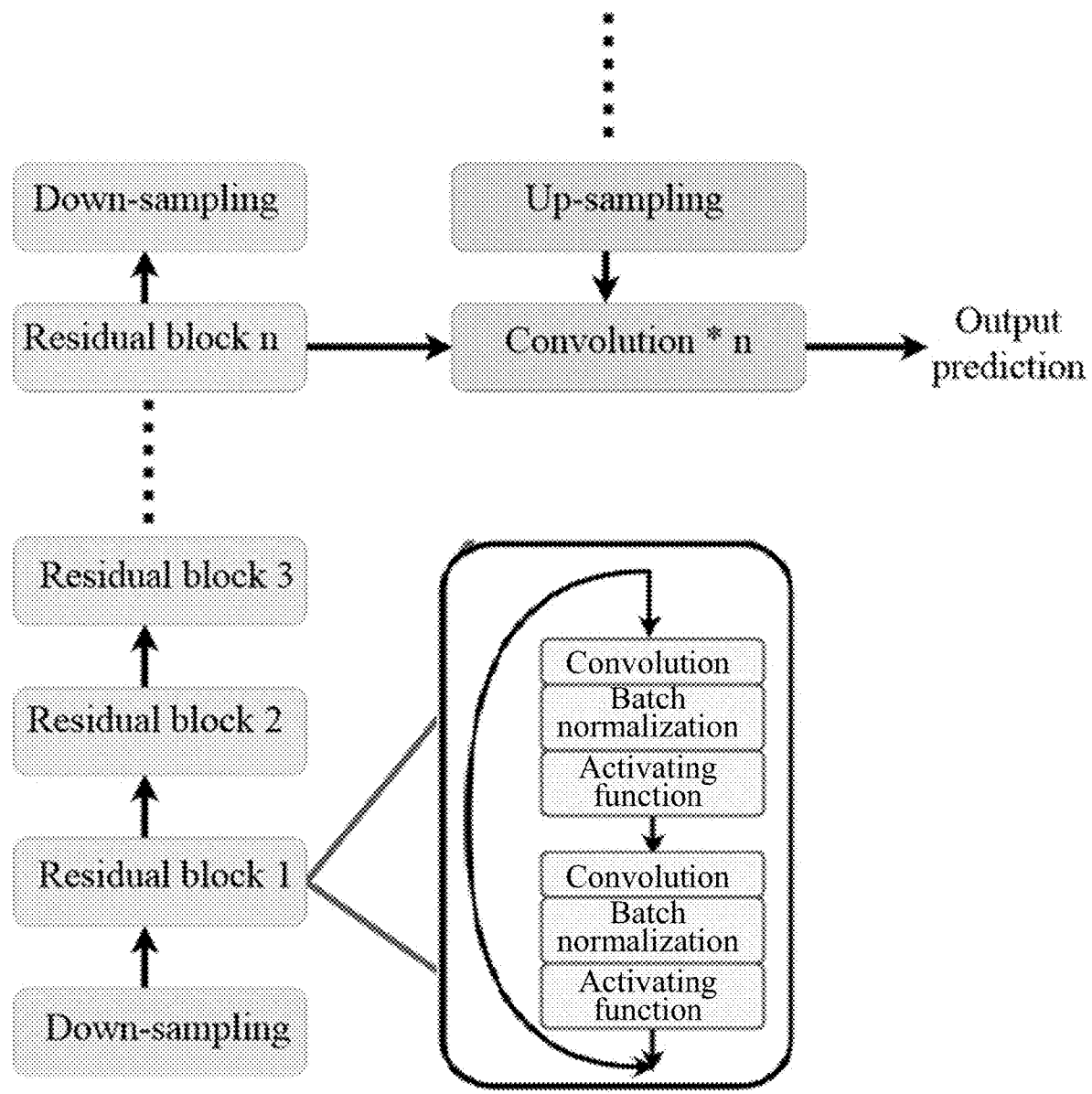
FIG. 3 is a schematic diagram of internal operations of each pyramid level according to the present invention.

FIG. 2 shows a design of the detection network, specifically:

1) Feature pyramid: After the feature extraction (backbone network) phase is over, different feature levels similar to a pyramid are formed through a plurality of up-sampling operations and lateral connections corresponding to a down-sampling stage of feature extraction, and a corresponding detection head is applied to each level to detect a cancerous region, which aims to adapt to cancerous regions of different sizes and traverse more suspected cancerous regions. FIG. 3 shows internal operations of each pyramid level.

2) Feature extraction: This stage includes a plurality of down-sampling processes (pooling layer), which aims to extract features in deeper semantics; all pooling layers are convolution operations with a kernel size of 3*3 and a step size of 2; and before down-sampling, each layer is composed of n residual blocks.

3) Residual block: There are two components inside that have the three operations of convolution, batch normalization, and activating function cascaded together, and a shortcut path that directly connects an internal input of a residual block to an output is added.

Figure 4:
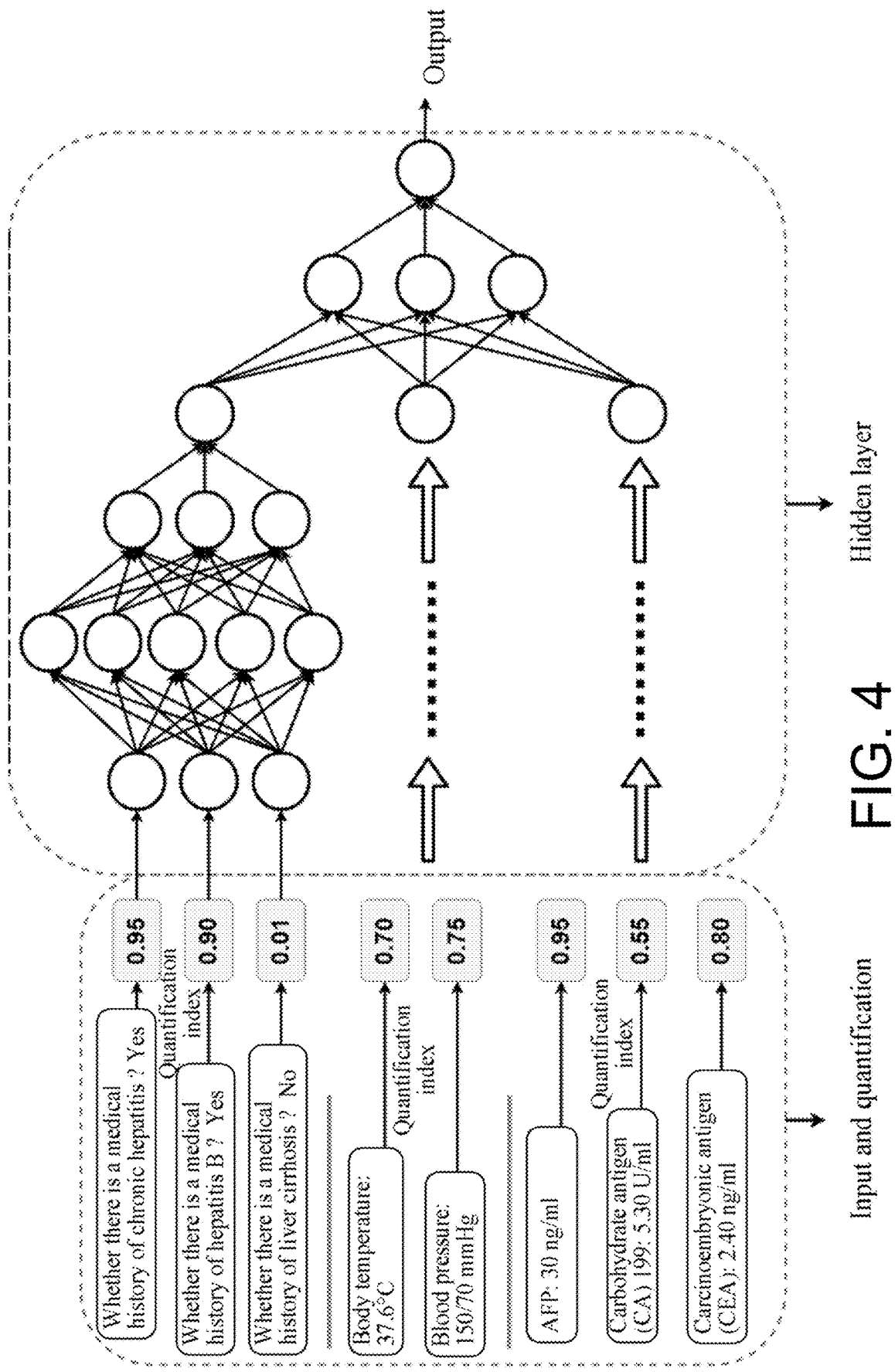
FIG. 4 is a schematic diagram of design steps of the clinical analysis network according to the present invention.

FIG. 4 shows a design of the clinical analysis network, specifically:

1) Input and quantification: After the clinical data acquisition is completed, a predetermined quantification index needs to be used to convert digital information under each index into a form that can be input by the clinical analysis network.

2) Hidden layer: The clinical data analysis network can be regarded as a large hidden layer (black box), and the network can be composed of a plurality of convolution modules (convolution+batch normalization+nonlinear activation, convolution layers are alternately provided with 1*1 and 3*3 convolution kernel size), residual blocks, or more complex network modules. An inside of the hidden layer can be divided into two parts. One part is for the separate forward propagation of quantitative data of medical history, physiological characteristics, and serum test of a patient (the figure merely shows some examples and there can be more items for each index, but once determined, the items cannot be arbitrarily changed later), which aims to learn a weight distribution of internal indexes for each of the three major clinical data sources. The other part is mainly for learning a weight distribution of the three major clinical data sources (that is, learning which index or which type of clinical data has a leading role in the assessment of a cancer risk level).

3) Output layer: After a plurality of fully connected layers are finally passed through in the hidden layer, an output predicted cancer probability value can be obtained. This value will play a key role in the subsequent prediction result weighting sub-module, and will be directly supervised by a true value (for example, a high risk value is 0.99) estimated by a physician during training.

A loss function of a CNN adopts the mean squared error (MSE):

$$MSE = \frac{1}{n}\sum_{i}^{n}(\hat{y}_i - y_i)^2$$

wherein n is a total number of samples in a training batch, $\hat{y}_i$ is a predicted value, and $y_i$ is a true value.

Step (2.2.2). Forward Inference and Prediction

Data in the test set divided in step (2.2.1) are fed to a trained neural network to predict bounding box coordinates of a cancerous region and a corresponding cancer confidence score based on the CT image data and to accordingly predict a cancer probability value of a corresponding patient based on the clinical data.

Step (3). Weighting for Prediction Results

A predicted cancer probability value obtained in step (2.2.2) is weighted to a predicted cancer confidence score to achieve a comprehensive determination of a cancerous region.

Step (3.1). All predicted detection boxes are truncated before post-processing.

In a detection network implemented by the present invention, each prediction output is encoded into $(N_{gx}*N_{gy}*N_A)$ vector with a length of 5, wherein $(N_{gx}*N_{gy})$ represents a total number of grids on a predicted feature map, $N_A$ represents a number of anchor boxes set in each grid, and the length of 5 refers to 4 bounding box attributes (center point coordinates, width, and height) and 1 target confidence score. In the present invention, truncation is conducted before an operation of the detection result post-processing sub-module (all vectors are read before being sent to the detection result post-processing sub-module), and confidence scores of all current detection boxes are retained to facilitate the comprehensive weighting with fused medical history, serum metabolism test information, and other features. The above vectors are sent to the subsequent detection result post-processing sub-module to complete the final visualization module output.

Step (3.2). Weighted Synthesis

A result of step (3.1) is weighted to a prediction output of the clinical analysis network to simulate an entire comprehensive detection process of early-stage (liver) cancer. Specifically, a threshold value of 0.5 is set for an output (a cancer probability value) of the clinical analysis network, a difference between the output and the threshold is stretched into an interval (0, 1), then an exponential function $e^x$ is used to acquire a scale factor, and the scale factor is applied to a confidence score output in step (3.1) to achieve incentive or penalty for the confidence score, as shown in the following formula:

$$conf = (P(\text{object}) * IOU(pred, gtBox)) \cdot f(e^{\sigma(P_{CA})});$$

$$IOU(pred, gtBox) = \frac{pred \cap gtBox}{pred \cup gtBox}$$

wherein a part on the left of ● in the above formula represents a confidence score output in step (3.1); P(object) represents an occurrence probability of a target (a cancerous region) in a prediction box; IOU represents a fit degree of a prediction box pred with a true box gtBox; a part on the right of ● in the above formula represents a scale factor; $P_{CA}$ represents a cancer probability value of a patient; and σ represents a normalization operation, that is, a difference between the cancer probability value and the threshold is stretched into an interval (0, 1).

Expected purpose of the incentive or penalty: Assuming that when a liver cancer (or another cancer) detection is finally performed, a confidence threshold is set as 0.2, and there is a prediction box with a confidence of 0.25 (which is actually a false positive, namely, error prediction), a scale factor is applied to the confidence for penalty (the patient has a low liver cancer probability), such that the confidence is reduced to 0.15 and becomes a true negative. That is, an image output prediction of a single detection network will be strengthened due to the comprehensive analysis of medical history and serum information. This is also in full compliance with a work flow of a physician in the detection of early-stage liver cancer. In some cases, it is ambiguous in images, but the clinical data analysis indicates a high cancer probability. In some cases, it cannot be determined based on clinical data analysis whether there is a cancer, but there are clear cancer manifestations in images. A comprehensive determination of a confidence score output and a target probability is the optimal solution.

Step (4). Post-processing of Detection Results

In the post-processing, repeated detection regions are screened out mainly through the non-maximum suppression (NMS) algorithm, and coordinates for a feature map size are mapped back to coordinates for an original image size.

The NMS algorithm is used to eliminate repeated detection boxes for the same target. After the execution is completed, except for a prediction box with the highest confidence threshold corresponding to a specified lesion region, all prediction boxes with an IOU higher than a preset IOU threshold will be filtered out.

Mapping coordinates for a feature map size back to coordinates for an original image size is also known as decoding a bounding box, which provides true coordinates on the original image for subsequent output visualization, thereby facilitating observation and display.

Step (5). Visualization of Detection Result Output

Figure 5:
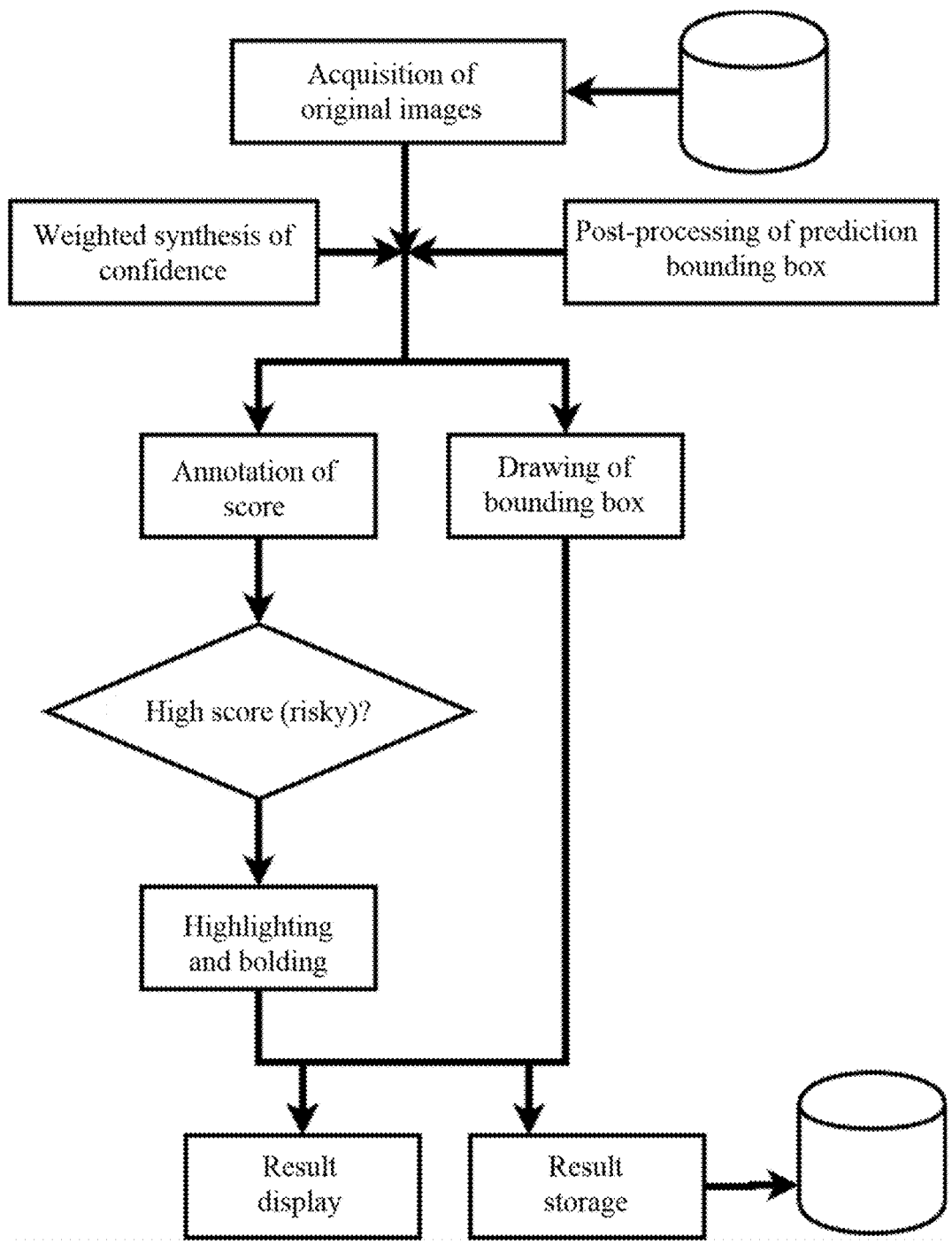
FIG. 5 is a flow chart of result output of the comprehensive detection according to the present invention.

This step includes: acquiring an original image, drawing a layer, and displaying an image, as shown in FIG. 5. Specifically:

Step (5.1). Original images at an input end of a detection network are directly acquired.

Step (5.2). Based on a score obtained after the weighted synthesis (including bounding box coordinates after the post-processing stage is completed), a corresponding rectangular box is drawn on an original image, and a weighted score is annotated on an upper left corner of a bounding box.

Step (5.3). After the comprehensive determination, additional highlighting is performed on a lesion region with a high cancer probability, which is convenient for the observation and further analysis of a physician. While displaying, data need to be saved in real time to a folder corresponding to a patient, which is convenient for the follow-up review of a physician.

Figure 6:
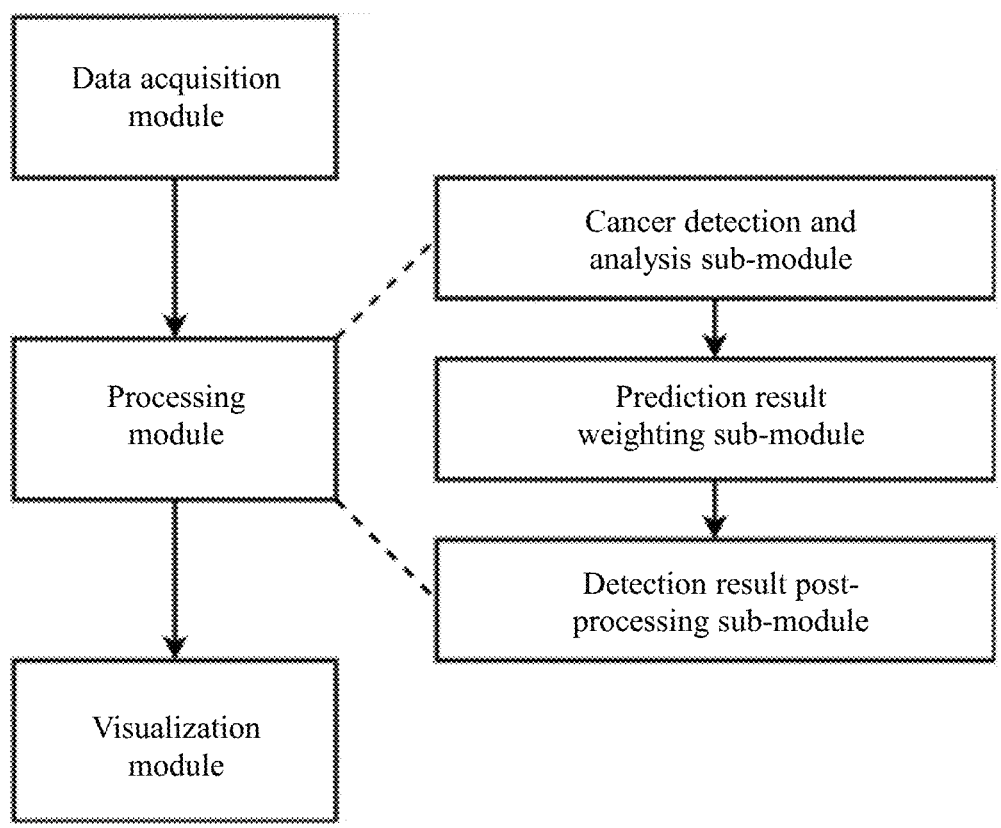
FIG. 6 is a schematic diagram of composition of the comprehensive detection device according to the present invention.

FIG. 6 shows a comprehensive detection device for a cancerous region, which includes a data acquisition module, a processing module, and a visualization module.

The data acquisition module is configured to acquire necessary image data and clinical text data from a daily workflow of a clinician to train a neural network, and establish a highly-organized data set reusable subsequently;

the processing module is configured to extract hidden features in the data and output a prediction;

the visualization module is configured to analyze an output prediction vector of the processing module and transmit the output prediction vector to a display to output and render a cancerous region and a corresponding confidence score of a current patient;

the processing module includes: a cancer detection and analysis sub-module configured to input acquired data into a CNN to generate a corresponding predicted value; a prediction result weighting sub-module configured to fuse a cancer probability value after feature extraction and a predicted cancer confidence score to improve the detection confidence; and a detection result post-processing sub-module configured to screen out repeated detection boxes for a same cancerous region and decode a bounding box.

Figure 7:
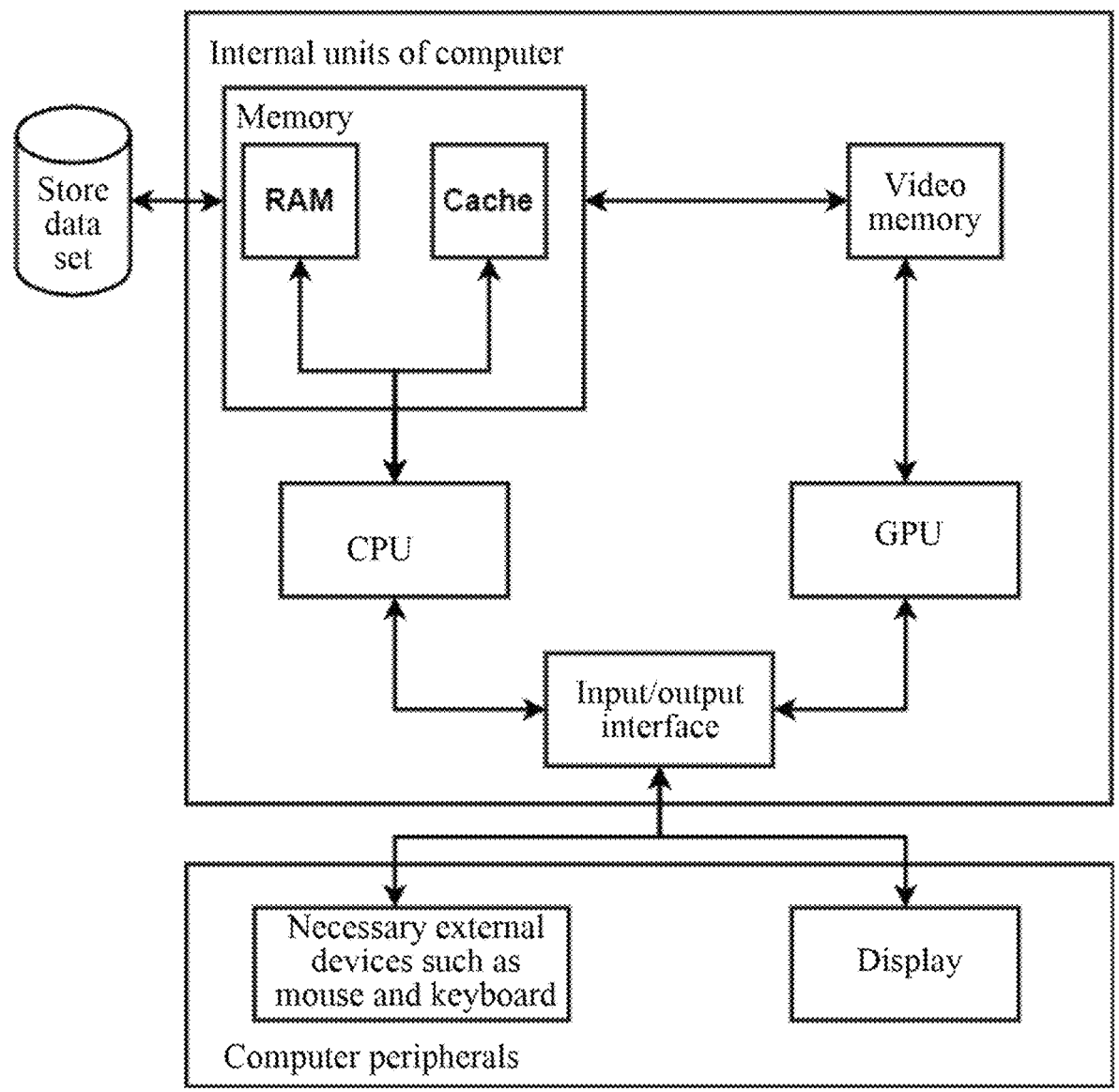
FIG. 7 is a schematic diagram of a structure of computer equipment running the comprehensive detection method according to the present invention.

FIG. 7 shows a structure of computer equipment running the comprehensive detection method according to the present invention, specifically including:

a display configured to visually output a comprehensive detection result to a graphics user interface (GUI); an input/output interface configured to connect various input and output devices; a memory configured to read out data in a stored data set, which are directly scheduled, processed, and stored by a central processing unit (CPU); a CPU configured to process raw data in the memory, including pre-processing image data and clinical text data in an early stage; a graphics processing unit (GPU) configured to accelerate the training of a neural network to improve the efficiency of complex gradient computation in a back propagation process, for example; and a video memory configured to store batch data transmitted from the memory.

The above examples are preferred implementations of the present invention, but the present invention is not limited to the above implementations. Any obvious improvement, substitution, or modification made by those skilled in the art without departing from the essence of the present invention should fall within the protection scope of the present invention.

What is claimed is:

1. A comprehensive detection method for a cancerous region, comprising:
   acquiring CT image data and clinical data;
   preprocessing the CT image data and the clinical data and converting the CT image data and the clinical data into a format being able to input applicable for a cancer detection and an analyzing sub-module;
   training a cancerous region detection network for preprocessed and annotated CT image data to predict bounding box coordinates of the cancerous region and a corresponding cancer confidence score;
   training a clinical analysis network for preprocessed clinical data with a cancer risk level to predict a cancer probability value of a corresponding patient;
   weighting a predicted cancer probability value to a predicted confidence score of the cancer to realize a comprehensive determination of the cancerous region, wherein a threshold value of 0.5 is set for the cancer probability value, a difference between the cancer probability value and the threshold is stretched into an interval (0, 1), then an exponential function $e^x$ is used to acquire a scale factor, and the scale factor is applied to the confidence score of the cancer to achieve incentive or penalty for the confidence score; and
   screening out repeated detection boxes for a same cancerous region and decoding a bounding box to output the cancerous region and a corresponding confidence score of a current patient;
   wherein the incentive or penalty is obtained by the following formula:

$$conf = (P(\text{object}) * IOU(pred, gtBox)) \cdot f\left(e^{\sigma(P_{CA})}\right)$$

$$IOU(pred, gtBox) = \frac{pred \cap gtBox}{pred \cup gtBox}$$

wherein (P(object)*IOU(pred,gtBox)) is a output of the confidence score, P(object) is an occurrence probability of the cancerous region in a prediction box pred; IOU represents a fit degree of the prediction box pred with a true box gtBox, $f(e^{\sigma(P_{CA})})$ is the scale factor, $P_{CA}$ is a cancer probability value of a patient, and σ represents a normalization operation, that is, a difference between the cancer probability value and the threshold is stretched into the interval (0, 1).

2. The comprehensive detection method for the cancerous region according to claim 1, wherein the cancer confidence score is retained by reading all vectors with a length of 5, and the length of 5 refers to 4 bounding box attributes and 1 target confidence score.

3. The comprehensive detection method for the cancerous region according to claim 1, wherein the detection network and the clinical analysis network are both convolutional neural networks (CNNs), and the training of the CNNs is achieved by a directional propagation learning method and a random gradient descent method.

4. The comprehensive detection method for the cancerous region according to claim 3, wherein the detection network forms different feature levels similar to a pyramid through a plurality of up-sampling operations and lateral connections corresponding to a down-sampling stage of feature extraction, and then achieves the detection of a cancerous region at the different levels; each pyramid level comprises a plurality of down-sampling, and each level is composed of n residual blocks before down-sampling; and the residual block comprises two components that have the three operations of convolution, batch normalization, and activating function cascaded together, and an internal input of the residual block is directly connected to an output.

5. The comprehensive detection method for the cancerous region according to claim 3, wherein the clinical analysis network comprises input and quantification, a hidden layer, and an output layer.

6. A comprehensive detection device for a cancerous region, comprising a data acquisition module, a processing module, and a visualization module,
    wherein the data acquisition module is configured to acquire CT image data and clinical data from a daily workflow of a clinician to train a neural network;
    the processing module is configured to extract hidden features in the data and output a prediction; and
    the visualization module is configured to output the cancerous region and a corresponding confidence score of a current patient;
    wherein the processing module comprises a cancer detection and analysis sub-module, a prediction result weighting sub-module, and a detection result post-processing sub-module;
    the cancer detection and analysis sub-module is configured to input acquired data into a CNN to generate a corresponding predicted value;
    the prediction result weighting sub-module is configured to fuse a cancer probability value after feature extraction and a predicted cancer confidence score; and
    the detection result post-processing sub-module is configured to screen out repeated detection boxes for a same cancerous region and decode a bounding box,
    wherein the prediction result weighting sub-module weights a predicted cancer probability value to a predicted confidence score of the cancer to realize a comprehensive determination of the cancerous region, wherein a threshold value of 0.5 is set for the cancer probability value, a difference between the cancer probability value and the threshold is stretched into an interval (0, 1), then an exponential function $e^x$ is used to acquire a scale factor, and the scale factor is applied to the confidence score of the cancer to achieve incentive or penalty for the confidence score;
    wherein the incentive or penalty is obtained by the following formula:

$$conf = (P(\text{object}) * IOU(pred, gtBox)) \cdot f\left(e^{\sigma(P_{CA})}\right)$$

$$IOU(pred, gtBox) = \frac{pred \cap gtBox}{pred \cup gtBox}$$

wherein (P(object)*IOU(pred,gtBox)) is a output of the confidence score, P(object) is an occurrence probability of the cancerous region in a prediction box pred; IOU represents a fit degree of the prediction box pred with a true box gtBox, $f(e^{\sigma(P_{CA})})$ is the scale factor, $P_{CA}$ is a cancer probability value of a patient, and $\sigma$ represents a normalization operation, that is, a difference between the cancer probability value and the threshold is stretched into the interval (0, 1).

7. A non-transitory computer-readable storage medium, wherein a computer program stored in the non-transitory computer-readable storage medium enables a processor to perform the comprehensive detection method for a cancerous region, wherein the comprehensive detection method for the cancerous region specifically comprising:
    acquiring CT image data and clinical data;
    preprocessing the CT image data and the clinical data and converting the CT image data and the clinical data into a format being able to input applicable for a cancer detection and an analyzing sub-module;
    training a cancerous region detection network for preprocessed and annotated CT image data to predict bounding box coordinates of the cancerous region and a corresponding cancer confidence score;
    training a clinical analysis network for preprocessed clinical data with a cancer risk level to predict a cancer probability value of a corresponding patient;
    weighting a predicted cancer probability value to a predicted confidence score of the cancer to realize a comprehensive determination of the cancerous region, wherein a threshold value of 0.5 is set for the cancer probability value, a difference between the cancer probability value and the threshold is stretched into an interval (0, 1), then an exponential function $e^x$ is used to acquire a scale factor, and the scale factor is applied to the confidence score of the cancer to achieve incentive or penalty for the confidence score; and
    screening out repeated detection boxes for a same cancerous region and decoding a bounding box to output the cancerous region and a corresponding confidence score of a current patient;
    wherein the incentive or penalty is obtained by the following formula:

$$conf = (P(\text{object}) * IOU(pred, gtBox)) \cdot f\left(e^{\sigma(P_{CA})}\right)$$

$$IOU(pred, gtBox) = \frac{pred \cap gtBox}{pred \cup gtBox}$$

wherein (P(object)*IOU(pred,gtBox)) is a output of the confidence score, P(object) is an occurrence probability of the cancerous region in a prediction box pred; IOU represents a fit degree of the prediction box pred with a true box gtBox, $f(e^{\sigma(P_{CA})})$ is the scale factor, $P_{CA}$ is a cancer probability value of a patient, and $\sigma$ represents a normalization operation, that is, a difference between the cancer probability value and the threshold is stretched into the interval (0, 1).

* * * * *